United States Patent
Lin et al.

(10) Patent No.: US 8,851,696 B2
(45) Date of Patent: Oct. 7, 2014

(54) FRAGRANCE LAMP STRUCTURE

(75) Inventors: Ming-Chuan Lin, Taichung (TW);
Kuo-Jui Huang, Taichung (TW);
Ying-Cheng Shih, Taichung (TW)

(73) Assignees: Dongguan Masstop Liquid Crystal Display Co., Ltd., Dongguan, Guangdong Province (CN); Wintek Corporation, Taichung (TW)

( * ) Notice: Subject to any disclaimer, the term of this patent is extended or adjusted under 35 U.S.C. 154(b) by 69 days.

(21) Appl. No.: 13/344,108

(22) Filed: Jan. 5, 2012

(65) Prior Publication Data
US 2012/0170291 A1    Jul. 5, 2012

(30) Foreign Application Priority Data
Jan. 5, 2011   (TW) .............................. 100100415 A

(51) Int. Cl.
*F21V 33/00* (2006.01)
*H01R 33/00* (2006.01)
*A62B 7/08* (2006.01)
*A61M 16/00* (2006.01)
*F24F 3/14* (2006.01)
*F24F 6/00* (2006.01)
*F21V 21/00* (2006.01)

(52) U.S. Cl.
CPC ....................................... *F21V 21/00* (2013.01)
USPC ............. 362/101; 362/96; 362/643; 362/644; 422/125; 392/393

(58) Field of Classification Search
USPC ........... 422/125; 392/393; 362/640–644, 161, 362/96, 101, 392–393, 253, 157
See application file for complete search history.

(56) References Cited

U.S. PATENT DOCUMENTS

| | | | |
|---|---|---|---|
| 5,902,552 A * | 5/1999 | Brickley | 422/121 |
| 6,609,842 B1 * | 8/2003 | Kimbrough | 398/195 |
| 8,110,835 B2 * | 2/2012 | Kumar et al. | 257/79 |
| 2006/0125420 A1 * | 6/2006 | Boone et al. | 315/291 |
| 2007/0076440 A1 * | 4/2007 | Chien | 362/643 |
| 2010/0260646 A1 * | 10/2010 | Jorgensen | 422/125 |

FOREIGN PATENT DOCUMENTS

TW           201100130           1/2011

OTHER PUBLICATIONS

English language translation of abstract of TW 201100130 (published Jan. 1, 2011).
English Abstract translation of TWM356511 (Published May 11, 2009).

* cited by examiner

*Primary Examiner* — Jong-Suk (James) Lee
*Assistant Examiner* — Alexander Garlen
(74) *Attorney, Agent, or Firm* — McClure, Qualey & Rodack, LLP

(57) ABSTRACT

A fragrance lamp structure including a carrying element, a lighting element and a driving element is provided. The carrying element has a carrying surface, a first contact surface and a second contact surface. The carrying surface and the first contact surface are opposite to each other, and so are the carrying surface and the second contact surface opposite to each other. The lighting element has a first heat output surface facing the first contact surface of the carrying element. The lighting element generates a first heat going through the first heat output surface and the first contact surface to heat up the carrying element. The driving element has a second heat output surface facing the second contact surface of the carrying element. The driving element generates a second heat going through the second heat output surface and the second contact surface to heat up the carrying element.

8 Claims, 3 Drawing Sheets

FRAGRANCE LAMP STRUCTURE

This application claims the benefit of Taiwan application Serial No. 100100415, filed Jan. 5, 2011, the subject matter of which is incorporated herein by reference.

BACKGROUND OF THE INVENTION

1. Field of the Invention

The invention relates in general to a fragrance lamp structure, and more particularly to a fragrance lamp structure which increases the adjustment margin of the heat source without incurring additional manufacturing costs.

2. Description of the Related Art

The fragrance lamp uses a container to carry the essential oil and heats up the essential oil with a candle so that the essential oil is volatilized in the air and fragrance is generated accordingly. Also, the candle of the fragrance lamp can be used for illumination purpose. However, there are many disadvantages when the candle is used as a heating source. The candle may easily be extinguished due to the flow of the air, and smokes or unpleasant odors may arise during combustion and cause air pollution. To the worse, if the candle is improperly used, fire may even occur and cause severe damage to life and wealth.

Besides, most of the heat generated during the combustion of the candle is conducted to the air, and only a part of the heat is conducted to the essential oil. Therefore, the above design is very inefficient in terms of heating.

Therefore, how to provide a safe fragrance lamp with high utilization rate of the heat but is free of air pollution has become a prominent task for the industries.

SUMMARY OF THE INVENTION

The invention is directed to a fragrance lamp structure, which largely increases energy utilization rate and adjustment margin through a structural design which fully utilizes the heat generated by the lighting element and the driving element without incurring additional manufacturing costs.

According to an aspect of the present invention, a fragrance lamp structure including a carrying element, a lighting element and a driving element is provided. The carrying element has a carrying surface, a first contact surface and a second contact surface adjacent to the first contact surface. The carrying surface and the first contact surface are opposite to each other, and so are the carrying surface and the second contact surface opposite to each other. The lighting element has a first heat output surface facing the first contact surface of the carrying element. The lighting element generates a first heat going through the first heat output surface and the first contact surface to heat up the carrying element. The driving element has a second heat output surface facing the second contact surface of the carrying element. The driving element generates a second heat going through the second heat output surface and the second contact surface to heat up the carrying element, wherein the driving element is electrically connected to the lighting element.

The above and other aspects of the invention will become better understood with regard to the following detailed description of the preferred but non-limiting embodiment (s). The following description is made with reference to the accompanying drawings.

DETAILED DESCRIPTION OF THE INVENTION

First Embodiment

Figure 1:
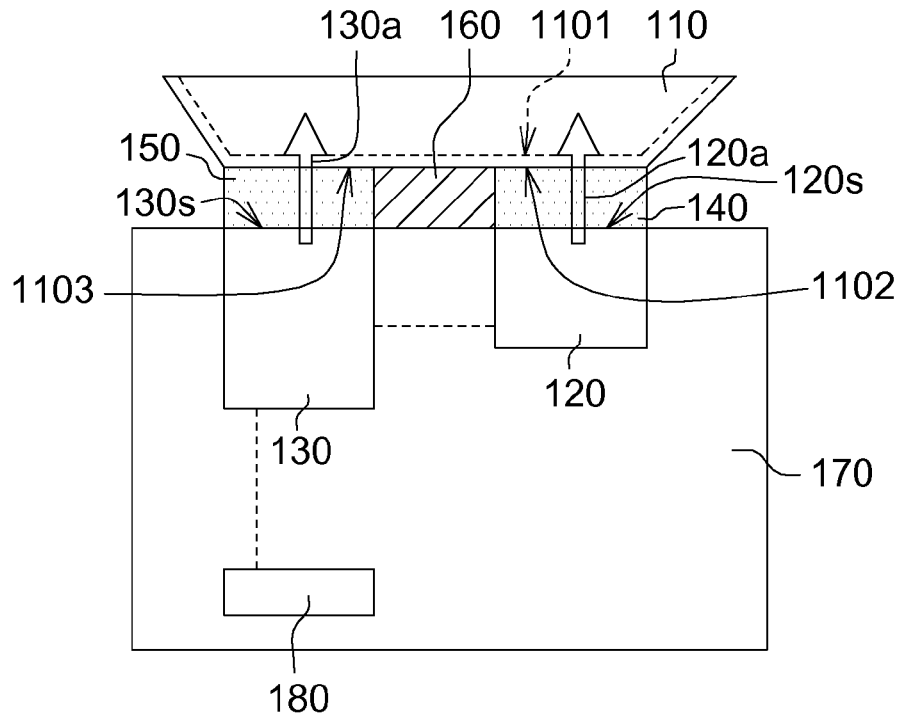
FIG. 1 shows a schematic diagram of a fragrance lamp structure according to a first embodiment of the invention.

Referring to FIG. 1, a schematic diagram of a fragrance lamp structure 10 according to a first embodiment of the invention is shown. The fragrance lamp structure 10 includes a carrying element 110, a lighting element 120, a driving element 130, a first thermal conductive element 140, a second thermal conductive element 150, a thermal insulation element 160, a foundation 170 and a control panel 180. The carrying element 110 is for placing a liquid or a solid (such as fragrant volatile agents or volatiles). The lighting element 120 for emitting a light is realized by such as a light emitting diode. The driving element 130 is electrically connected to the lighting element 120 for driving the lighting element 120 to generate light and heat. The control panel 180 is such as a rotation button or several press keys for controlling the light and the heat generated by the lighting element 120 and the driving element 130. The elements of the fragrance lamp structure 10 are further elaborated below.

In the present embodiment of the invention, the carrying element 110 realized by such as a dish-shaped container has a carrying surface 1101, a first contact surface 1102 and a second contact surface 1103 adjacent to the first contact surface 1102. The carrying surface 1101 and the first contact surface 1102 are opposite surfaces, and so are the carrying surface 1101 and the second contact surface 1103 opposite to each other, wherein the carrying element 110 is made from a thermal conductive material such as metal or ceramics.

The lighting element 120 is embedded in the foundation 170, and a first heat output surface 120s of the lighting element 120 is exposed. The driving element 130 is embedded in the foundation 170, and a second heat output surface 130s of the driving element 130 is exposed.

The first thermal conductive element 140 is disposed between the lighting element 120 and the carrying element 110. The first thermal conductive element 140 has two opposite surfaces respectively attached to the first heat output surface 120s of the lighting element 120 and the first contact surface 1102 of the carrying element 110, wherein the first heat output surface 120s faces the first contact surface 1102. The second thermal conductive element 150 is disposed between the driving element 130 and the carrying element 110. The second thermal conductive element 150 has two opposite surfaces respectively attached to the second heat output surface 130s of the driving element 130 and the second contact surface 1103 of the carrying element 110, wherein the second heat output surface 130s faces the second contact surface 1103. In other words, the lighting element 120 and the driving element 130 respectively are adjacent to and facing the first contact surface 1102 and the second contact surface 1103 of the carrying element 110.

The first thermal conductive element 140 and the second thermal conductive element 150 can be made from a composite material containing metal, a ceramic, or a thermal conductive plastic, or a thermal conductive glue or a thermal conductive pad. Thus, a first heat 120a generated by the lighting element 120 can be easily conducted to the carrying element 110 through the first heat output surface 120s, the first thermal conductive element 140 and the first contact surface 1102. Likewise, a second heat 130a generated by the driving element 130 can be easily conducted to the carrying element 110 through the second heat output surface 130s, the second thermal conductive element 150 and the second contact surface 1103. Thus, the carrying element 110 not only receives the first heat 120a generated when the lighting element 120 is activated but also receives the second heat 130a generated when the driving element 130 is activated, so that the fragrance lamp structure 10 has larger flexibility in controlling the fragrant volatile agents or volatiles located on the carrying surface 1101 of the carrying element 110.

Figure 2:
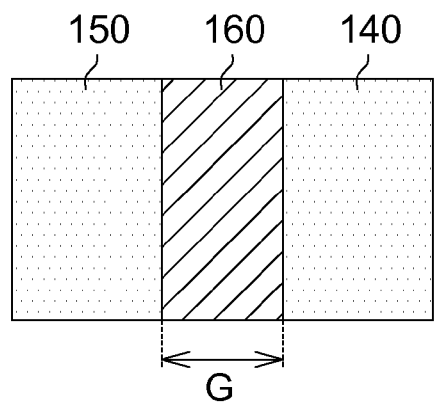
FIG. 2 shows a top view of the first thermal conductive element, the second thermal conductive element and the thermal insulation element of FIG. 1.

Referring to FIG. 1 and FIG. 2. FIG. 2 shows a top view of the first thermal conductive element 140, the second thermal conductive element 150 and the thermal insulation element 160 of FIG. 1. In the present embodiment of the invention, the thermal insulation element 160 is disposed between the first thermal conductive element 140 and the second thermal conductive element 150 for separating the first thermal conductive element 140 from the second thermal conductive element 150. That is, the thermal insulation element 160 makes the first thermal conductive element 140 and the second thermal conductive element 150 separated by a distance G. The first thermal conductive element 140 and the second thermal conductive element 150 have lower thermal resistance. If the first thermal conductive element 140 and the second thermal conductive element 150 are not separated by the thermal insulation element 160 and contact each other instead, most of the thermal flow will circulate between the first thermal conductive element 140 and the second thermal conductive element 150, and most of the thermal flow cannot be conducted to the carrying element 110 for volatizing the volatiles located on the carrying element 110. Thus, the first heat 120a and the second heat 130a generated by the lighting element 120 or the driving element 130 cannot be fully utilized.

Suppose the first thermal conductive element 140 and the second thermal conductive element 150 are not separated by the thermal insulation element 160 and contact each other instead. Meanwhile, the elements with higher temperature (such as the driving element 130) will transmit the heat to the elements with lower temperature (such as the lighting element 120) through the first thermal conductive element 140 and the second thermal conductive element 150. Thus, a part of the heat generated by the lighting element 120 and the driving element 130 cannot be conducted to the carrying element 110. To the worse, when the heat is conducted to an element with relatively lower temperature, the element with relatively lower temperature may be damaged due to temperature increase, and the lifespan may even be shortened. In an alternative embodiment, the thermal insulation element 160 may be removed and replaced by air which is itself an excellent insulation medium.

Figure 3:
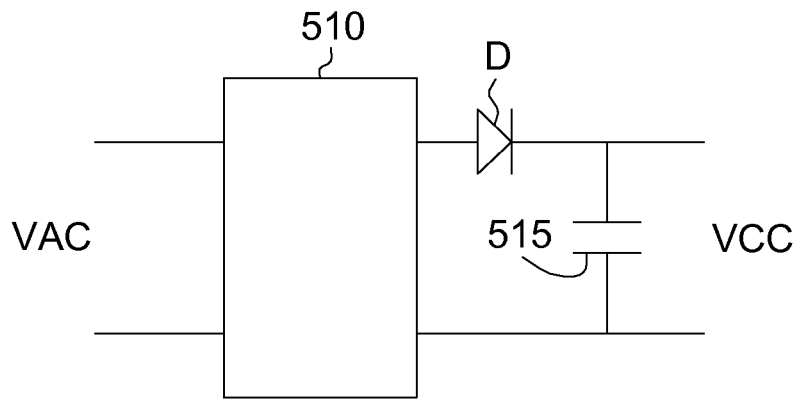
FIG. 3 shows a power circuit diagram of the fragrance lamp structure of FIG. 1.

Referring to FIG. 3, a power circuit diagram of the fragrance lamp structure of FIG. 1 is shown. After the AC voltage VAC is applied to the transformer 510 and stepped down, the AC voltage VAC is converted into a DC voltage with ripples by a rectified diode D. Then, the ripples are filtered by a filtering capacitor 515 to obtain a stable DC voltage VCC provided to the lighting element 120 such as the driving circuit indicated in FIG. 4.

Figure 4:
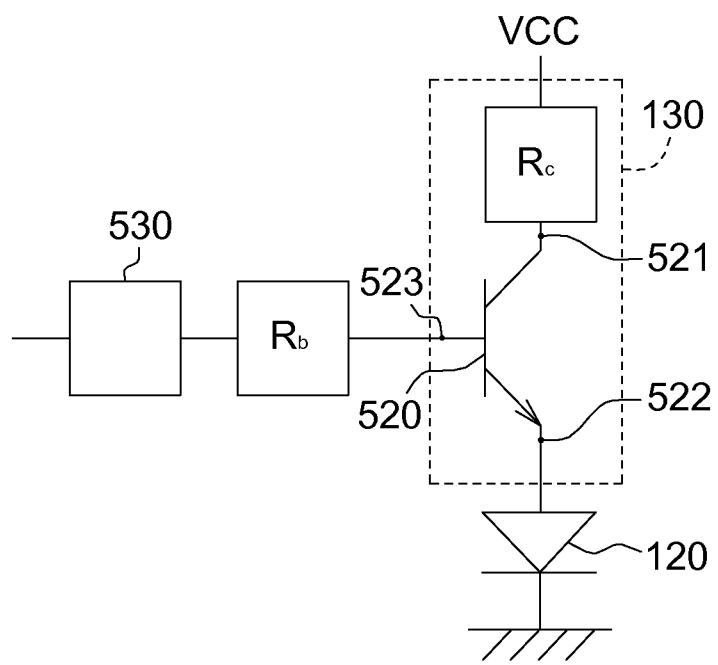
FIG. 4 shows a driving circuit diagram of the fragrance lamp structure of FIG. 1.

Referring to FIG. 4. The driving circuit includes a lighting element 120 and a driving element 130. The driving element 130 further includes a bipolar junction transistor (BJT) 520 and a collector resistor Rc. The BJT 520 has a collector 521, an emitter 522 and a base 523. The collector 521 is electrically connected to one end of the collector resistor Rc, and the other end of the collector resistor Rc is electrically connected to the DC voltage VCC. In other words, the collector 521 electrically connects the collector resistor Rc in serial, and the collector resistor Rc electrically connects the DC voltage VCC in serial. The emitter 522 is electrically connected to the lighting element 120. The base 523 is electrically connected to one end of the base resistor Rb, and the other end of the base resistor Rb is electrically connected to pulse width modulation (PWM) control unit 530. In other words, the base 523 electrically connects the base resistor Rb in serial, and the base resistor Rb electrically connects the PWM control unit 530 in serial.

Thus, the PWM control unit 530 controls the magnitude of the voltage of the base 523. By controlling the magnitude of the voltage of the base 523, the magnitude of the current flowing to the emitter 522 from the collector 521 can be controlled. In other words, the magnitude of the current flowing to the lighting element 120 from the DC voltage VCC is controlled for electrically connecting the control panel 180 to the PWM control unit 530, so that the user can operate the rotation button or press keys on the control panel 180 (Referring to FIG. 1) for changing the voltage of the base 523 by controlling the PWM control unit 530. Meanwhile, the DC voltage VCC electrically connected to the collector 521, according to the magnitude of the voltage of the base 523, enables corresponding magnitude of current to flow to the lighting element 120 electrically connected to the emitter 522 so that the lighting element 120 illuminates the light and generates the heat. Thus, the amounts of the heat generated by the lighting element 120 and the driving element 130 can be respectively determined according to the magnitude of the current flowing thereto. Thus, the amounts of the heat generated by the lighting element 120 and the driving element 130 and the luminous intensity of the lighting element 120 can be controlled to achieve desired levels by operating the control panel 180.

Second Embodiment

Figure 5:
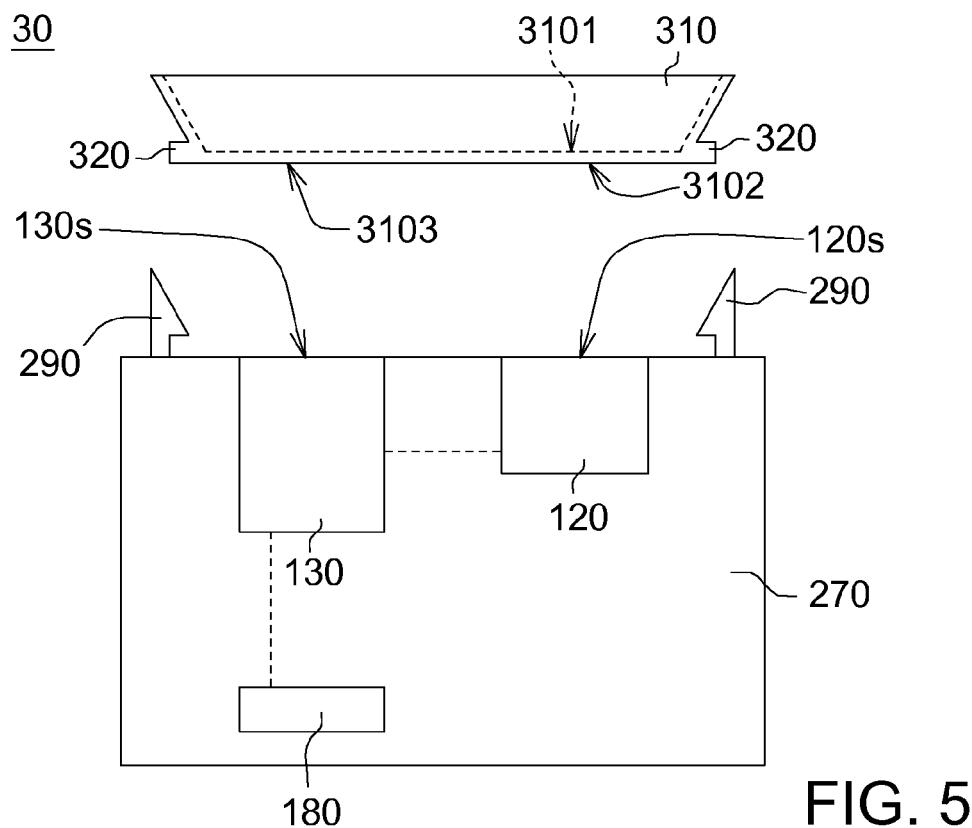
FIG. 5 shows a decomposition diagram of a fragrance lamp structure according to a second embodiment of the invention.

Referring to FIG. 5, a decomposition diagram of a fragrance lamp structure 30 according to a second embodiment of the invention is shown. The fragrance lamp structure 30 of the present embodiment of the invention is different from the fragrance lamp structure 10 of the first embodiment in that the fragrance lamp structure 30 of the present embodiment of the invention does not adopt the first thermal conductive element 140, the second thermal conductive element 150 and the thermal insulation element 160, but directly assemble the carrying element 310 and the foundation 270 by way of mutual engaging, and other similarities are not repeated.

The carrying element 310 of the present embodiment of the invention has a carrying surface 3101, a first contact surface 3102 and a second contact surface 3103 adjacent to the first contact surface 3102. The carrying surface 3101 and the first contact surface 3102 are opposite to each other, and the carrying surface 3101 and the second contact surface 3103 are opposite to each other. The carrying element 310 includes two locking elements, such as two protrusions 320. In an alternative embodiment, the locking elements of the carrying element 310 can be designed as hook and groove. The two protrusions 320 are extended outwards from the carrying element 310 and located on two opposite sides of the carrying element 310. Also, the foundation 270 of the present embodiment of the invention includes two locking pieces 290 located on the foundation 270 and facing the carrying element 310.

The position of each locking piece 290 substantially corresponds to the position of each protrusion 320.

Figure 6:
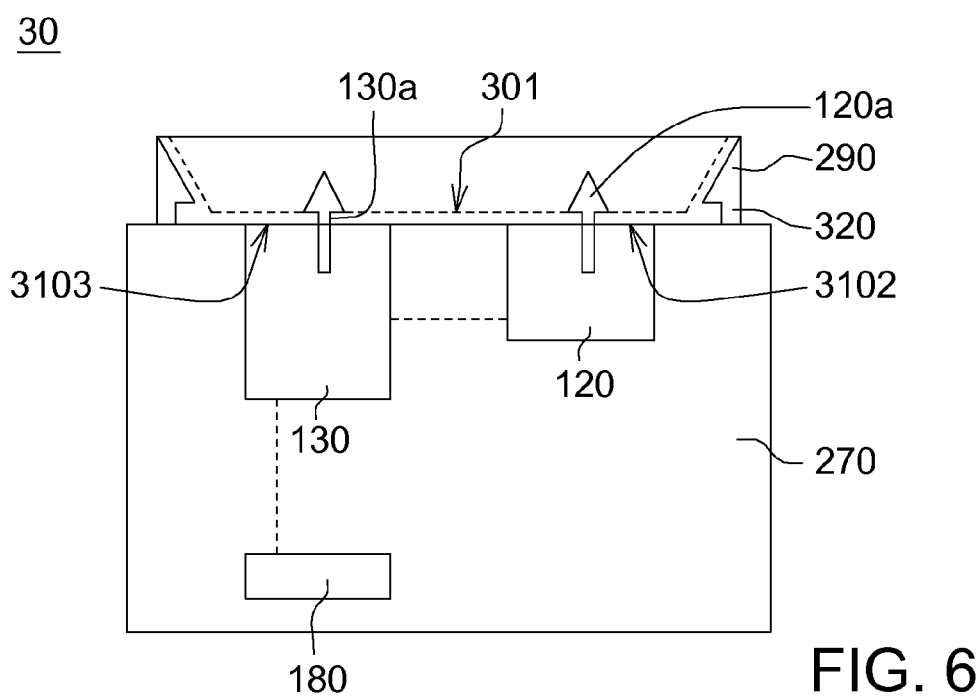
FIG. 6 shows an assembly diagram of the fragrance lamp structure of FIG. 5.

Referring to FIG. 6, an assembly diagram of the fragrance lamp structure of FIG. 5 is shown. The locking piece 290 has elasticity. When the carrying element 310 is moved towards the foundation 270, the locking piece 290 is pushed outwards by the protrusion 320 and slightly deformed until the first contact surface 3102 and the second contact surface 3103 of the carrying element 310 are attached to the first heat output surface 120s of the lighting element 120 and the second heat output surface 130s of the driving element 130 respectively, and then the locking piece 290 is restored to the initial position and locked on the protrusion 320. Meanwhile, the carrying element 310 and the foundation 270 are mutually engaged through the locking piece 290 and the protrusion 320, so that the lighting element 120 and the driving element 130 are tightly attached to the first contact surface 3102 and the second contact surface 3103 of the carrying element 310 respectively. Thus, the first heat 120a generated when the lighting element 120 functions can be conducted to the carrying element 310 through the first heat output surface 120s and the first contact surface 3102. The second heat 130a generated when the driving element 130 functions can be conducted to the carrying element 310 through the second heat output surface 130s and the second contact surface 3103. That is, the first heat 120a and the second heat 130a generated when the lighting element 120 and the driving element 130 function can respectively be conducted to the carrying element 310 directly.

According to the fragrance lamp structure disclosed in the above embodiments of the invention, the heat generated by the lighting element and the driving element is used for heating up the to-be-heated material on the carrying element. Most of the heat generated by the fragrance lamp structure is fully utilized. Moreover, the driving element is an existing element of the fragrance lamp structure, and no additional cost is needed. The fragrance lamp structure includes a thermal insulation element disposed between the first thermal conductive element and the second thermal conductive element, so that the heat generated by the lighting element and the driving element can be gathered and conducted to the carrying element instead of being conducted to the other side and causing heat loss. As the to-be-heated material is volatilized, the heat generated by the fragrance lamp structure can be removed and will not be left on the fragrance lamp structure to avoid thermal deformation occurring to the material, light decay occurring to the lighting element and thermal damage occurring to the electronic elements, hence prolonging the lifespan of the fragrance lamp structure.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A fragrance lamp structure, comprising: a carrying element having a carrying surface, a first contact surface and a second contact surface adjacent to the first contact surface, wherein the carrying surface and the first contact surface are opposite to each other, and the carrying surface and the second contact surface are opposite to each other;
   a lighting element having a first heat output surface facing the first contact surface of the carrying element, wherein the lighting element generates a first heat going through the first heat output surface and the first contact surface to heat up the carrying element;
   a driving element having a second heat output surface facing the second contact surface of the carrying element, wherein the driving element generates a second heat going through the second heat output surface and the second contact surface to heat up the carrying element, and the driving element is electrically connected to the lighting element, the first heat and the second heat are determined according to the magnitude of a current flowing thereto by controlling a voltage of the driving element;
   a first thermal conductive element disposed between the lighting element and the carrying element, wherein the first thermal conductive element comprises two opposite surfaces in direct contact with the first heat output surface of the lighting element and the first contact surface of the carrying element respectively;
   a second thermal conductive element disposed between the driving element and the carrying element, wherein the second thermal conductive element comprises two opposite surfaces in direct contact with the second heat output surface of the driving element and the second contact surface of the carrying element respectively; and
   a thermal insulation element disposed between the first thermal conductive element and the second thermal conductive element for separating the first thermal conductive element from the second thermal conductive element.

2. The fragrance lamp structure according to claim 1, further comprising:
   a foundation, wherein the lighting element is embedded in the foundation, the first heat output surface of the lighting element is exposed, the first heat output surface of the lighting element is attached to one of the two opposite surfaces of the first thermal conductive element, the driving element is embedded in the foundation, the second heat output surface of the driving element is exposed, and the second heat output surface of the driving element is attached to one of the two opposite surfaces of the second thermal conductive element.

3. The fragrance lamp structure according to claim 1, wherein the driving element comprises a bipolar junction transistor (BJT) and a collector resistor, the BJT has a base, a collector and an emitter, the collector electrically connects the collector resistor in serial, the collector resistor electrically connects the power in serial, the emitter is electrically connected to the lighting element, and the fragrance lamp structure further comprises a pulse width modulation (PWM) control unit electrically connected to the base.

4. The fragrance lamp structure according to claim 1, wherein the carrying element is made from a thermal conductive material.

5. The fragrance lamp structure according to claim 1, wherein the first thermal conductive element and the second thermal conductive element are made from a ceramics, a thermal conductive plastics or a thermal conductive glue.

6. A fragrance lamp structure, comprising:
   a carrying element having a carrying surface, a first contact surface and a second contact surface adjacent to the first contact surface, wherein the carrying surface and the first contact surface are opposite to each other, and the carrying surface and the second contact surface are opposite to each other;
   a lighting element having a first heat output surface facing the first contact surface of the carrying element, wherein the lighting element generates a first heat going through the first heat output surface and the first contact surface to heat up the carrying element, and wherein the first heat output surface of the lighting element is in direct contact with the first contact surface of the carrying element; and a driving element having a second heat output surface facing the second contact surface of the carrying element, wherein the driving element generates a second heat going through the second heat output surface and the second contact surface to heat up the carrying element, the driving element is electrically connected to the lighting element, the first heat and the second heat are determined according to the magnitude of a current flowing thereto by controlling a voltage of the driving element, and the second heat output surface of the driving element is in direct contact with the second contact surface of the carrying element.

7. The fragrance lamp structure according to claim 6, further comprising:

a foundation, wherein the lighting element is embedded in the foundation, the first heat output surface of the lighting element is exposed, the first heat output surface of the lighting element is attached to the first contact surface of the carrying element, the driving element is embedded in the foundation, the second heat output surface of the driving element is exposed, and the second heat output surface of the driving element is attached to the second contact surface of the carrying element.

8. The fragrance lamp structure according to claim 7, wherein the foundation comprises a plurality of first locking elements, the carrying element comprises a plurality of second locking elements, the positions of the first locking elements correspond to that of the second locking elements, and each first locking element and the corresponding second locking element are mutually engaged.

* * * * *